United States Patent
Corbett et al.

(10) Patent No.: US 7,616,734 B1
(45) Date of Patent: Nov. 10, 2009

(54) MULTI-STEP METHOD OF NONDESTRUCTIVELY MEASURING A REGION WITHIN AN ULTRA-HARD POLYCRYSTALLINE CONSTRUCTION

(75) Inventors: Loel Gene Corbett, Saratoga Springs, UT (US); Nephi Mourik, Provo, UT (US)

(73) Assignee: Smith International, Inc., Houston, TX (US)

( * ) Notice: Subject to any disclaimer, the term of this patent is extended or adjusted under 35 U.S.C. 154(b) by 172 days.

(21) Appl. No.: 11/745,958

(22) Filed: May 8, 2007

Related U.S. Application Data

(60) Provisional application No. 60/799,137, filed on May 9, 2006.

(51) Int. Cl.
*G01N 23/223* (2006.01)

(52) U.S. Cl. .......................................... 378/46; 378/50

(58) Field of Classification Search ............. 378/44–50; 209/588–589

See application file for complete search history.

(56) References Cited

U.S. PATENT DOCUMENTS

| 5,603,414 | A | 2/1997 | Rooney et al. | 209/588 |
| 5,835,205 | A | 11/1998 | Hunter et al. | 356/30 |
| 6,544,308 | B2 | 4/2003 | Griffin et al. | 51/309 |
| 7,196,782 | B2 * | 3/2007 | Fielden et al. | 356/72 |

* cited by examiner

*Primary Examiner*—Courtney Thomas
(74) *Attorney, Agent, or Firm*—Connolly Bove Lodge & Hutz LLP

(57) ABSTRACT

A method for nondestructively obtaining measurement information of a region within one or more ultra-hard polycrystalline constructions comprises conducting a first measurement using x-ray fluorescence by directing x-rays onto a surface of the diamond body, receiving x-ray fluorescence from the diamond body, and deriving measurement information regarding the region therefrom. A second method can be used on the same or other ultra-hard polycrystalline constructions to obtain measurement information regarding the region in a manner that is relatively more time efficient than the first method to facilitate use of the measurement method on a large number of constructions. The second measurement can be selected from the group including beta backscatter, x-ray radioscopy, eddy current, magnetic induction, and microresistance. In an example embodiment, the method is used to determine the thickness of a region within the diamond body that comprises less catalyst material than another region within the body.

12 Claims, 9 Drawing Sheets

MULTI-STEP METHOD OF NONDESTRUCTIVELY MEASURING A REGION WITHIN AN ULTRA-HARD POLYCRYSTALLINE CONSTRUCTION

RELATION TO COPENDING PATENT APPLICATION

This patent application claims the benefit of priority from U.S. Provisional Patent Application Ser. No. 60/799,137, filed May 9, 2006, which is incorporated herein in its entirety.

FIELD OF THE INVENTION

This invention relates to nondestructive methods developed for measuring the thickness or variation in thickness of a region within a material microstructure and, more specifically, to a multi-step method of measuring the thickness or variation in thickness of one or more region in ultra-hard polycrystalline constructions.

BACKGROUND OF THE INVENTION

The formation of constructions having a material microstructure made up or two or more different layers or regions of materials is well known. Such constructions are intentionally engineered in this fashion to provide a desired mix of physical, mechanical and/or thermal properties within the material microstructure, making it better equipped to handle a particular end use application. In order to provide such desired properties in a predictable and consistent manner, the thickness or variation of thickness of each engineered region must be controlled.

It is, therefore, necessary that the thickness of each such region within the construction be measured for the purpose of both controlling the process that is used to make the construction, to ensure its consistency and for controlling the quality or ability of the construction to perform as expected. Methods useful for measuring the thickness or variation in the thickness of a region within a material construction will vary depending on the nature of the construction. For material constructions used in tooling, wear, and cutting applications provided in the form of an ultra-hard polycrystalline material, e.g., comprising polycrystalline diamond, a useful method for measuring the thickness or variation of thickness of one or more region within the construction is by destructive method or destructive testing.

Destructive testing requires that the construction itself be cut or otherwise treated in a manner that physically exposes the different regions therein so that they can be measured by visual inspection. In an example embodiment, where the construction is one comprising an ultra-hard polycrystalline material such as diamond or cubic boron nitride, the construction itself is cut, e.g., in half, so that the different regions forming the construction can be viewed visually for purposes of measuring the thickness or variation of thickness of the regions. In an example embodiment, such visual indication is made with the assistance of a magnifying device such as a microscope, e.g., a scanning electron microscope.

While such destructive test method is useful for determining the thickness or variation of thickness within a construction, it is time consuming in that after the part is cut it must usually be further prepared by grinding, polishing or the like, then mounted for microscopic evaluation, and the microscopic evaluation must be taken over a number of different points to gather sufficient data to arrive at a numerical value, e.g., an average region thickness throughout the part. Further, the use of such destructive test method is expensive, and results in the parts that are measured being destroyed, thereby adversely impacting the economics of making the parts.

It is, therefore, desired that a method be developed that is capable of measuring the thickness or variation of thickness within a region of a material construction, e.g., an ultra-hard polycrystalline construction, in a manner that is not destructive. It is further desired that such a method be capable of providing such a desired measurement in a manner that has a consistent degree of accuracy. It is further desired that the method be capable of providing an indication of the region thickness at different locations within the construction, and enable efficient testing on a large-scale production basis.

SUMMARY OF THE INVENTION

A method for nondestructively obtaining measurement information, according to principles of this invention, as it relates to a particular region or interface within an ultra-hard polycrystalline construction. In an example embodiment, the ultra-hard polycrystalline construction comprises a polycrystalline diamond body, and the measurement information relates to a region within the polycrystalline diamond body that comprises less catalyst material than otherwise present in another region of the polycrystalline diamond body.

In an example embodiment, the method comprises conducting a first measurement by using x-ray fluorescence by directing x-rays onto a surface of the diamond body, receiving x-ray fluorescence from the diamond body, and deriving measurement information from the received x-ray fluorescence. In an example embodiment, the x-rays are provided to cause target atoms in the diamond body to emit x-ray fluorescence, and in a preferred embodiment, the region comprising less catalyst material comprises less target atoms. Accordingly, target atoms include those materials selected from Group VIII elements of the Periodic table. This first measurement technique can be used to determine the interface of the region comprising less catalyst material, and to provide measurement information sufficient to generate a plot or map of the interface along a desired surface area.

A second measurement technique can be used to conduct a second measurement on the same ultra-hard polycrystalline construction or on another ultra-hard polycrystalline construction, wherein the other ultra-hard polycrystalline construction can be produced in the same batch as the one measured using the first measurement technique, thus being expected to have a measured interface that is generally similar to that of the construction measured by the first measurement technique. In an example embodiment, it is desired that the second measurement technique be one that can provide measurement information relatively more quickly than the first measurement technique to facilitate the measurement of a number of constructions. Thus, in a preferred embodiment, the second measurement technique is different than that used to conduct the first measurement, and can be one selected from the group consisting of beta backscatter, x-ray radioscopy, eddy current, magnetic induction, and microresistance.

In an example embodiment, the region comprising less catalyst material extends a depth from a surface of the diamond body, and the remaining region of the diamond body includes the catalyst material. The measurement information is provided to determine the thickness of the region comprising less of the catalyst material. The method of this invention enables one to obtain measurement information regarding a region within an ultra-hard polycrystalline construction in a nondestructive manner that is accurate, and that can be implemented on a large scale to provide such measurement information for a plurality of such constructions in a manner that is relatively time efficient.

BRIEF DESCRIPTION OF THE DRAWINGS

These and other features and advantages of the present invention will be appreciated as the same becomes better understood by reference to the following detailed description when considered in connection with the accompanying drawings wherein.

DETAILED DESCRIPTION OF THE INVENTION

A nondestructive method useful for determining the thickness or variation of thickness within an ultra-hard polycrystalline construction, according to the principles of this invention, is one using two or more different nondestructive measurement techniques. In an example embodiment, a first nondestructive measurement technique used is X-ray fluorescence (XRF). As described in greater detail below, XRF is used to provide detailed thickness and/or variation in thickness information within a targeted region of the ultra-hard polycrystalline construction in a manner that is accurate and that does not result in the destruction of the part. If desired, XRF can be used to generate thickness information for an entire region within the construction and produce a topographic map illustrating the thickness and any variation in thickness along this region.

In an example embodiment, a second nondestructive measurement technique or method is used for the purpose of screening large numbers of parts, e.g., ones that are of a family of parts, wherein at least one part of the family has already been measured by the XRF method. The second nondestructive measurement technique is preferably one that can be performed relatively more quickly than XRF to facilitate the rapid measurement of many parts, and thus one that would be suitable for measuring a large number of parts in production to provide an indication whether the target region thickness for each measured part meets a desired target or set point thickness. In an example embodiment, the second nondestructive measurement technique can be performed using Beta Backscatter (BB). In another example embodiment, the second nondestructive measurement technique can be performed using X-ray Radioscopy (XRR).

Figure 1:
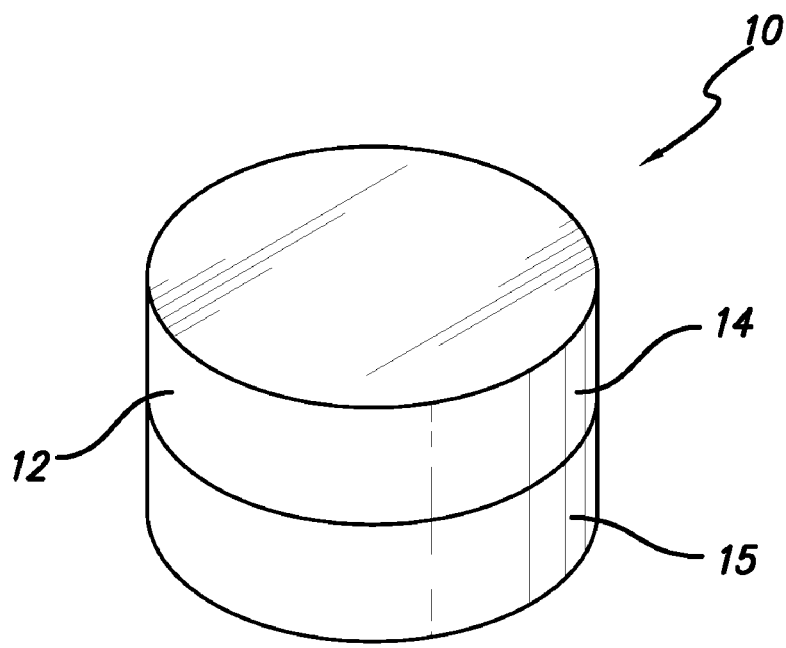
FIG. 1 is schematic view of an ultra-hard polycrystalline construction provided in the form of a compact.

FIG. 1 illustrates an ultra-hard polycrystalline construction 10. The construction generally comprises a body 12 formed from an ultra-hard polycrystalline material 14, e.g., comprising diamond, polycrystalline diamond (PCD), cubic boron nitride (cBN), polycrystalline cubic boron nitride (PcBN), and mixtures thereof. The body 12 may or may not be attached to a substrate. In the example embodiment illustrated in FIG. 1, the construction includes a substrate 15 that is joined together with the body 12 to form a compact.

The substrate can be formed from a variety of different materials such as those useful for forming conventional PCD compacts, like ceramic materials, metallic materials, cermet materials, carbides, nitrides, and mixtures thereof. When the ultra-hard polycrystalline construction comprises polycrystalline diamond, a preferred substrate material comprises cemented tungsten carbide (WC—Co).

Figure 2:
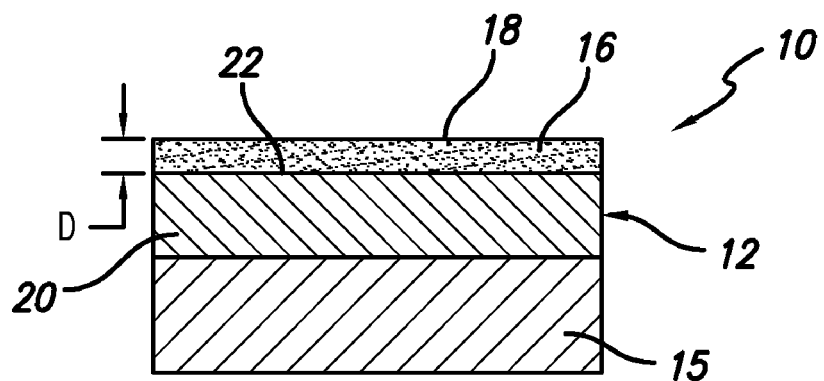
FIG. 2 is a cross-sectional side view of the ultra-hard polycrystalline construction taken along a section of FIG. 1.

FIG. 2 illustrates a cross-sectional view of a section taken through the ultra-hard polycrystalline construction 10 of FIG. 1, illustrating the material microstructure of the construction and its different regions. In an example embodiment, the body 12 includes a first region 16, that extends a depth "D" into the body from a outside body surface 18, and a second region 20, that extends from the first region 16 to the substrate 15. An interface 22 within the body defines the point of transition between the first and second regions 16 and 20.

While a particular polycrystalline construction 10 has been illustrated in FIG. 2, having first and second regions occupying particular locations of the construction, it is to be understood that constructions having first and second regions that are positioned differently than that illustrated in FIG. 2 can also be measured using the methods of this invention. For example, nondestructive measuring methods of this invention can be used for measuring regions in an ultra-hard polycrystalline construction that are positioned at locations other than on the construction front side surface or table, e.g., along a sidewall surface of the construction.

In an example embodiment the body 12 is formed from PCD and the first region 16 includes PCD that has been treated so that it is substantially free of a catalyst material, e.g., a solvent metal catalyst, used to form the PCD. As used herein, the term "substantially free" is understood to mean that the catalyst material is removed from the first region, in which case the first region has a material microstructure comprising a polycrystalline diamond matrix phase and a plurality of voids interposed therebetween. The term "substantially free" is also understood to include treatments that render the catalyst material used to form the PCD no longer catalytic, such as by reacting the catalyst material to form a noncatalytic compound and/or by encapsulating the catalyst material with another material that prevents the catalyst material from functioning as a catalyst with the polycrystalline diamond matrix phase when the construction is subjected to a cutting, tooling or wear application.

The catalyst material used to form the diamond phase in the construction microstructure can be the same as that used to form conventional PCD by high pressure/high temperature (HPHT) sintering process. Such catalyst materials include metals from Group VIII of the Periodic table, with cobalt (Co) being the most common. In an example embodiment, the catalyst material is a solvent metal catalyst such as Ni, Co, Fe, and combinations thereof. The catalyst material can be removed by chemical, electrical, or electrochemical processes. In an example embodiment, the catalyst material is Co and is removed from the first region by acid leaching process.

In an example embodiment, it is desired that the depth "D" of the first region within the body be controlled to provide consistent and repeatable characteristics of mechanical and thermal performance for the construction. As explained in greater detail below, it is therefore necessary to develop an accurate and repeatable technique for measuring the depth of the first region in the construction to ensure the consistency of such desired performance characteristics.

In an example construction, the body second region 20 comprises PCD that includes the catalyst material. The second or PCD region 20 has a material microstructure comprising a polycrystalline diamond matrix and the catalyst material disposed interstitially within the matrix. In an example embodiment, the substrate 15 is attached to the body 12 at the interface with the body second region 20.

The depth of the first region can be controlled by adjusting one or more parameters of the process that are used to treat the first region to render it substantially free of the catalyst material. Once a desired depth is achieved, e.g., to meet the desired performance characteristics for a particular end use application, the process is carefully controlled so that the first region depth in all remaining parts within the family of parts (made from the same material and processed in the same manner) is the same. As noted above, a current method that is used for measuring the depth of the body first region is by destructive testing, whereby the part is cut in half, polished or otherwise prepared, and then is viewed and measured using a scanning electron microscope.

While this technique enables one to determine the depth of the first region with some degree of accuracy, it also results in the destruction of the part, which adversely impacts manufacturing costs and efficiency. Additionally, this process is time consuming as the user typically measures the depth of the first region along the entire part diameter, and then takes the average of the measured points to arrive at the overall part average thickness of the first region.

While the use of such destructive testing method is effective for determining the average depth of the first region 16 in the body of the destroyed part, using such method on a regular basis is not practical for a large scale manufacturing processes due to both the large number of parts destroyed, and the time involved with preparing and measuring each such part. Ideally, it is desired that a measurement technique or method be adopted that permits the measurement of as many parts produced within a family as possible for the purpose of ensuring the performance characteristics of such part.

Additionally, the use of such destructive testing technique enables one to only view the region depth at one location within the part and is not useful in identifying any depth irregularities that may exist along the entire interface between the first and second regions, which depth irregularities (whether patterned or random) may have an unwanted impact the desired performance characteristics of the part.

XRF is a technique that can be used to nondestructively measure the depth of one or more identified regions in the construction in a manner that is accurate, and that is capable of providing depth information across the entire region or surface area being measured. XRF relies on bombarding a target material with x-ray energy provided from an x-ray excitation source such as an e-ray tube or a radioactive source. Once the x-ray enters the material it is either absorbed by a target atom or scattered through the material.

When the x-ray is absorbed by a target atom, the atom transfers all of its energy to an innermost electron, which mechanism is referred to as the "photoelectric effect." During this process, if the primary x-ray has sufficient energy, electrons are ejected from the inner shells of the atom, creating vacancies or voids in the vacated shells. These vacancies present an unstable condition for the atom.

Electrons from the atom's outer shells are transferred to the inner shells to return the atom to a stable condition. The process of electron transfer from the outer shell to the inner shell produces a characteristic x-ray having an energy that is the difference between the two binding energies of the corresponding shells. The x-rays emitted by the target atom during this process are called X-ray fluorescence (XRF). The process of detecting and analyzing the emitted x-rays from the targeted atoms is called XRF analysis. Depending on the particular application, XRF can be produced by using not only x-rays but also by using other primary excitation sources like alpha particles, photon, or high-energy electron beams.

The energy level or wavelength of fluorescent x-rays emitted by the target atom within the material is proportional to the atomic number of the target atom, and is characteristic for a particular material. The quantity of energy release via such emitted fluorescent x-rays is also dependent upon the thickness or depth of the material being measured.

Figure 3:
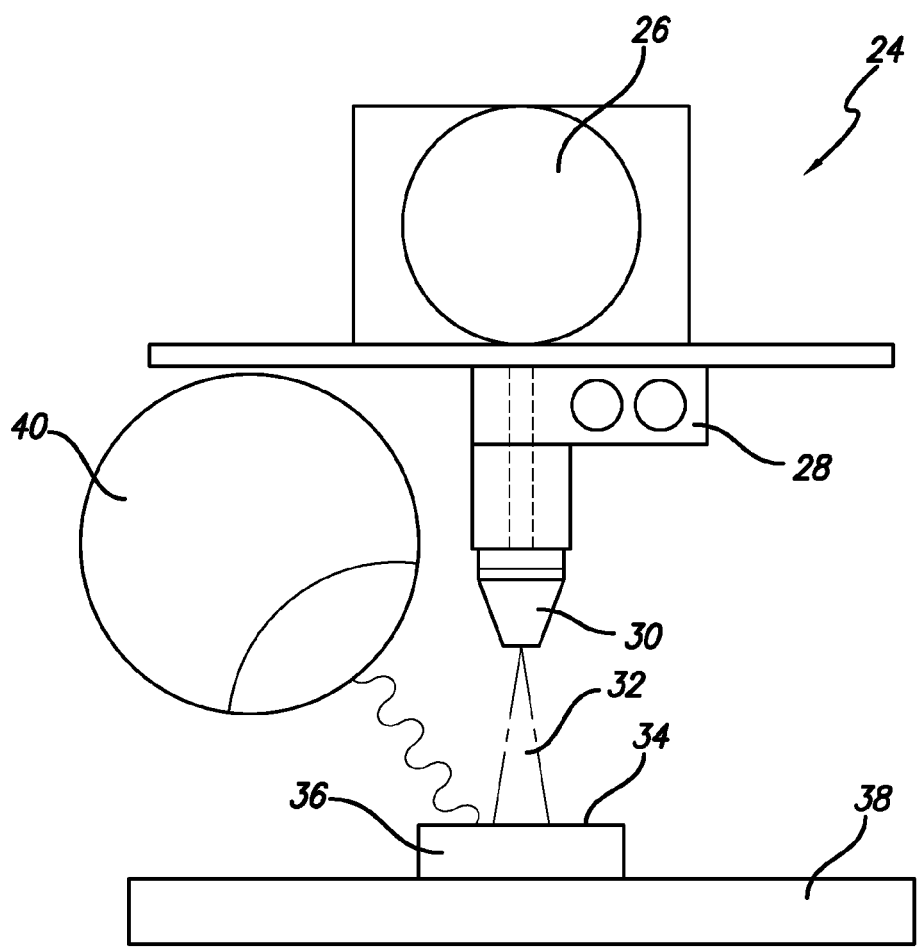
FIG. 3 is a schematic side view of an X-ray fluorescence device useful for determining the thickness and/or variations in thickness of a region within the ultra-hard polycrystalline construction of FIGS. 1 and 2.

FIG. 3 illustrates an XRF device 24 as used to measure the depth of one or more regions in the ultra-hard polycrystalline construction of FIGS. 1 and 2. In an example embodiment, the device 24 comprises an x-ray source 26 and can include a fail-safe shutter 28 and a collimator 30. The collimator is used to direct an incident x-ray 32 onto a desired surface 34 of the ultra-hard polycrystalline construction 36 that is positioned on a suitable positioning assembly 38. In an example embodiment, the positioning assembly and/or the x-ray source can be configured to move if necessary to provide extended coverage over a desired region of the ultra-hard polycrystalline construction 36.

The device 24 further includes a proportional counter 40 that may be part of or separate from the device. The proportional counter may comprise a gas disposed within a counter tube, which gas is ionized by the emission of x-rays or photons from the target material. The emitted x-rays or photons ionize gas in the counter tube that is proportional to their energy, permitting spectrum analysis for determining the nature of the target material and its thickness.

In an example embodiment, the ultra-hard polycrystalline construction 36 is oriented with the device 24 so that the device emits x-ray energy onto the surface 34 of the ultra-hard polycrystalline construction from which the body first region extends. The device is configured having an x-ray source 26 selected to produce x-ray energy that will create a void in the inner shell of the catalyst material that is present in the body second region. In an example embodiment, the catalyst material is cobalt. In the event that the catalyst material in the second region is some other material, the x-ray source is selected to create a void in the inner shell of such other catalyst material.

In an example embodiment, the device is configured to emit x-rays onto a designated surface area of the ultra-hard polycrystalline construction to produce XRF from the targeted atoms, e.g., the catalyst material in the second region, within such designated surface area. X-rays that are generated by the device pass through the ultra-hard polycrystalline construction body first region and to the target atoms in the second region. The XRF emitted from the targeted atoms in the portion of the second region associated with the designated surface area is measured. In an example embodiment, the XRF emitted is an indication of the distance from the surface 34 of the ultra-hard polycrystalline construction to the second region, or the thickness or depth of the first region.

This measurement data can be used to generate a plot of the first region thickness within the designated surface area. The device can be repositioned relative to the construction and used multiple times to emit x-rays onto other surface areas of the ultra-hard polycrystalline construction to obtain desired measurement data and plot the first region thickness or depth at a number of different surface areas. Generally speaking, the surface area of the target material that is covered by the device in one instance will vary depending on the size of the collimator. The larger the collimator the larger the surface area being covered, and the fewer number of times that the device will need to be repositioned and used to generate measurement data sufficient to cover the entire surface area of the target material, if such is desired.

In an example embodiment, XRF is used as a first method or technique for nondestructively obtaining measurement data of an ultra-hard polycrystalline construction first region thickness or depth. XRF is preferably used as the first method because of its ability to provide measurement data for the entire surface area of the first region, that can be plotted to produce a topographical view of the interface between the first and second regions within the construction.

Such a topographical view can be very helpful in identifying any irregularities along the entire interface, i.e., in the first region thickness or depth, that could exist and possibly be the source of an undesired performance characteristic. Additionally, the use of such a topographical plot can help to identify whether any such irregularities are in a arranged in pattern or are random, which can be useful for the purpose of evaluating and/or controlling the process that is used to form the ultra-hard polycrystalline construction, e.g., to form the body first region.

Figure 4:
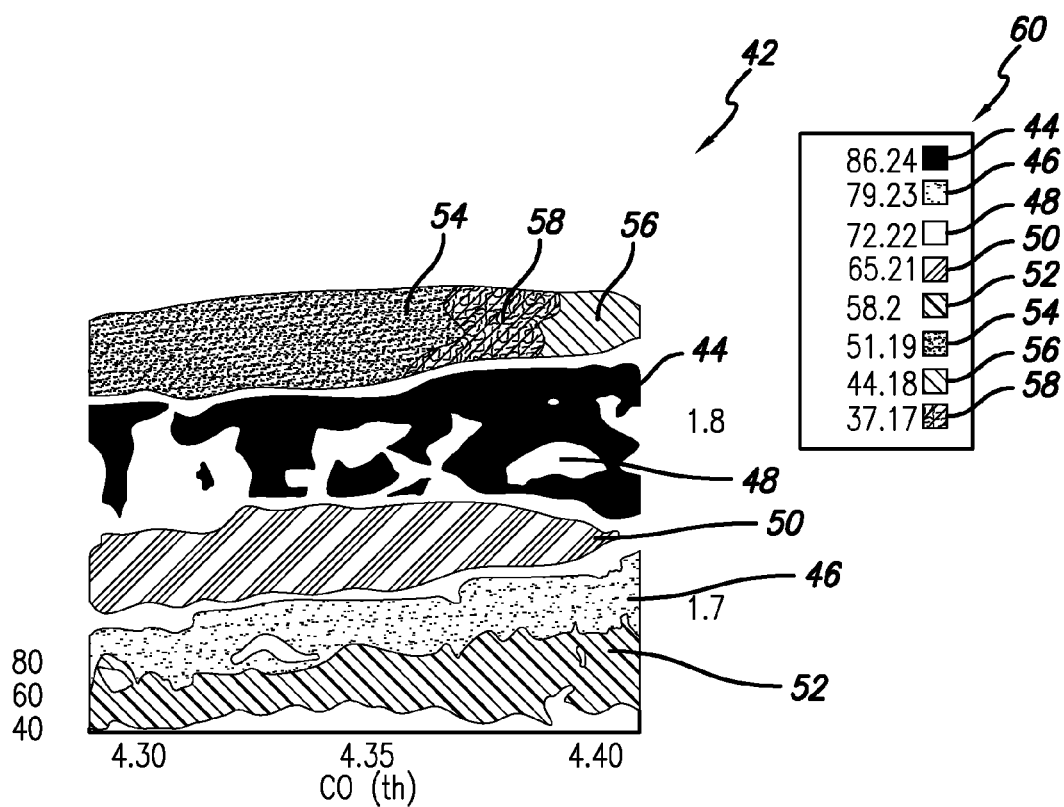
FIG. 4 is a measurement result taken from the X-ray fluorescence device of FIG. 3.

FIG. 4 illustrates a plot 40 that is generated by using the XRF device of FIG. 3. The plot provides a topographical visual indication of the depth along a portion of the body first region (or the distance from the surface of the ultra-hard polycrystalline construction to the second region) within a predetermined surface area. In this example, the XRF device was used to generate a 400 point array scan of a surface area of the ultra-hard polycrystalline construction comprising a body having a polycrystalline diamond matrix first region substantially free of a catalyst material, and a PCD second region that includes a cobalt catalyst material, wherein the target atom is cobalt. The designated surface area had a size of approximately 0.1 by 0.025 inches.

As illustrated in the plot 40, different depths along portion of the first region within this surface area are indicated by differently colored regions 44, 46, 48, 50, 52, 54, 56 and 58. In an example embodiment, a legend 60 is provided to match the colors of the plot to a corresponding numerical thickness. In the example embodiment that is illustrated, the numerical data provided in the legend is provided in dimensions of micrometers.

In an example embodiment, XRF is used as a first nondestructive test method for obtaining measurement data for the first region of an ultra-hard polycrystalline construction representing a product family. More preferably, XRF is used as the first test method to obtain sufficient measurement data to provide a plot of the first region thickness. Generation of the plot, such as that illustrated in FIG. 4, is used to evaluate whether there are any unwanted irregularities in the depth of the first region that could impair product performance. Once the plot is generated, and the first region depth is determined to be within an acceptable standard, then the first region thickness for a number of products in the same product family, i.e., products that are produced from the same materials and in the same general manner, are subsequently measured using a second nondestructive measurement method.

The second nondestructive measurement method is preferably one that demonstrates a good degree of accuracy, and can be used to relatively quickly evaluate the thickness of a part to permit obtaining part first region thickness information on a number of parts in a relatively short amount of time. In an example embodiment, the second nondestructive measurement method can be used on a designated number of parts within the part family, or on each part within the part family, to further ensure that the first region thickness or depth of the parts within a family is within a designated tolerance.

Figure 5:
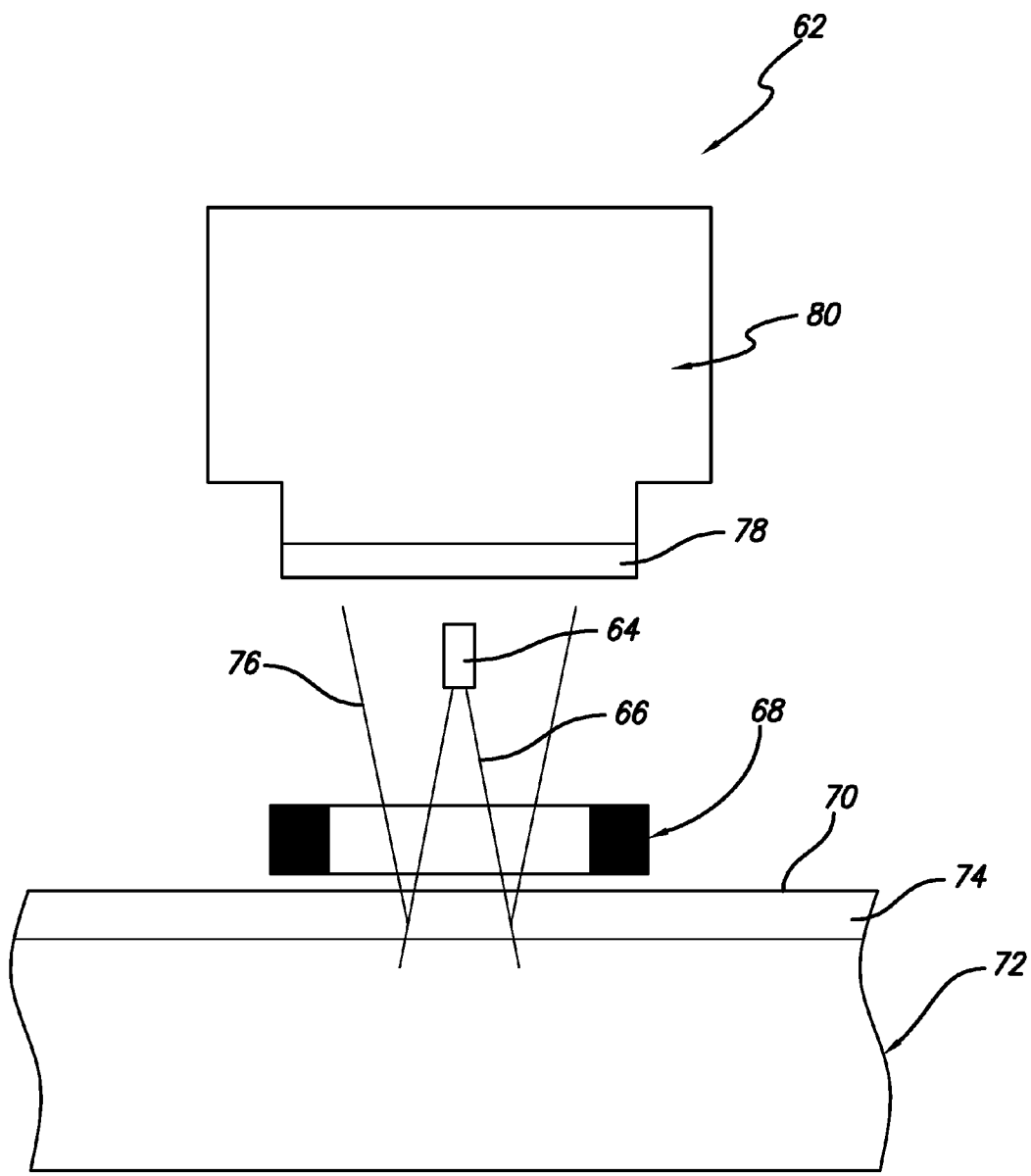
FIG. 5 is a schematic view of a Beta Backscatter device useful for determining the thickness and/or variation in thickness of a region within the ultra-hard polycrystalline construction of FIGS. 1 and 2.

A first example second nondestructive measurement method or technique useful with this invention is Beta Backscatter (BB). Referring to FIG. 5, BB uses a device 62 that includes a radiation source 64 in the form of a beta-emitting isotope that is positioned to direct a beam of beta particles 66 through an aperture 68. In an example embodiment, the radiation source and aperture can be packaged or combined together in the form of a probe. The device aperture 68 is positioned onto a surface 70 of the ultra-hard polycrystalline construction 72 is adjacent the first region 74. When the device is actuated, the beta particles 66 enter the construction first region 74 and a proportion of the beta particles are "backscattered" from the construction. The backscattered particles 76 pass back through the aperture 68.

The backscattered particles 76 penetrate a very thin window 78 of a Geiger Muller tube 80. The Geiger Muller tube 80 contains a gas that ionizes when the backscattered beta particles pass through the window. This ionization causes a momentary discharge to occur across electrodes (not shown) disposed within the Geiger Muller tube 80. The discharge is in the form of a pulse, and the device is configured to count the pulses and translate them into a thickness measurement of the construction first region 74

Generally, materials with low atomic numbers backscatter the beta particles at a significantly lower rate than materials with high atomic numbers. When used with the ultra-hard polycrystalline material, beta particles are scattered by both materials in the first region and the materials beneath the second region, (Please confirm that this statement is correct), and the material in the first region has an atomic number that is different from that of the material in region beneath the first region (Please confirm that this statement is correct). If the thickness of the first region changes, so does the backscatter rate. The change in the rate of particles scattered is therefore a measure of the coating thickness.

In an example embodiment, before the BB method of measuring is placed into operation the device is calibrated by using a standard in the form of a construction having a known first region thickness. Once the BB device is calibrated it is placed into use to measuring the construction first region thickness. A feature of using BB as the second nondestructive measurement method is that once calibrated, it can be provide a first region thickness measurement more quickly than by using XRF, making it well suited for use production.

The number of parts in a family that are measured using BB, as well as the number of locations on a part that are measured to provide an indication of the measured thickness for a part, will depend on a number of factors such as the nature of the part itself, and/or the size of the BB probe or aperture, and/or the stability of the process used to make the parts. For example, depending on the particular material microstructure of the ultra-hard polycrystalline construction and/or possible known irregularities in the first region thickness, e.g., as identified using XRF, it may be necessary to use BB to take measurement data at more that one location on the part to obtain an average first region thickness for the part.

The number of parts in a family that are measured, or the frequency of part sample measurement in a family, using BB may be influenced by the stability of the process used to make the parts. Generally, the more stable the process used to make the parts in a family the fewer the number of parts to be measured using this second nondestructive method to obtain a desired level of certainty that the first region thickness of the parts meets a predetermine standard.

Figure 6:
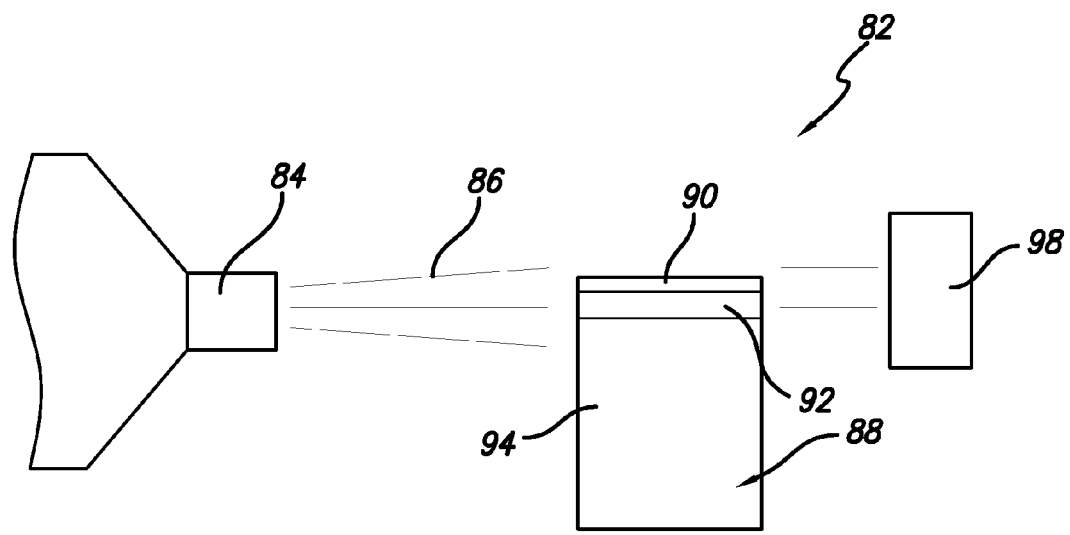
FIG. 6 is a schematic view of an X-ray radioscopy device useful for determining the thickness and/or variation in thickness of a region within the ultra-hard polycrystalline constructions of FIGS. 1 and 2.

A second example second nondestructive measurement method or technique useful with this invention is X-ray radioscopy (XRR). Referring to FIG. 6, XRR uses a device 82 that includes a radiation source 84 that is constructed to emit and direct X-ray wavelength electromagnetic radiation 86 onto a designated target. For use in this invention, the radiation source 84 is positioned generally perpendicular to the ultra-hard polycrystalline construction 88. In an example embodiment, the X-ray source 84 is positioned to direct X-ray radiation 86 in a direction perpendicular to the ultra-hard polycrystalline construction, and specifically perpendicular to the first region 90.

As the X-rays pass through the construction, the different regions of the construction, e.g., the first region 90, the second region 92, and the substrate 94, absorb different amounts of the X-ray radiation, thus allow respectively different amounts of the X-ray radiation to pass therethrough. The X-ray radiation 96 existing the construction is passed to a detecting source 98. In an example embodiment, the detecting source can be provided in the form of photographic film, semiconductor plates, image intensifiers, or electronic hardware capable of creating, displaying and/or storing an electronic image of the X-rayed construction. Thus, the XRR device is configured to produce a visual image of the construction showing its different regions.

Figure 7:
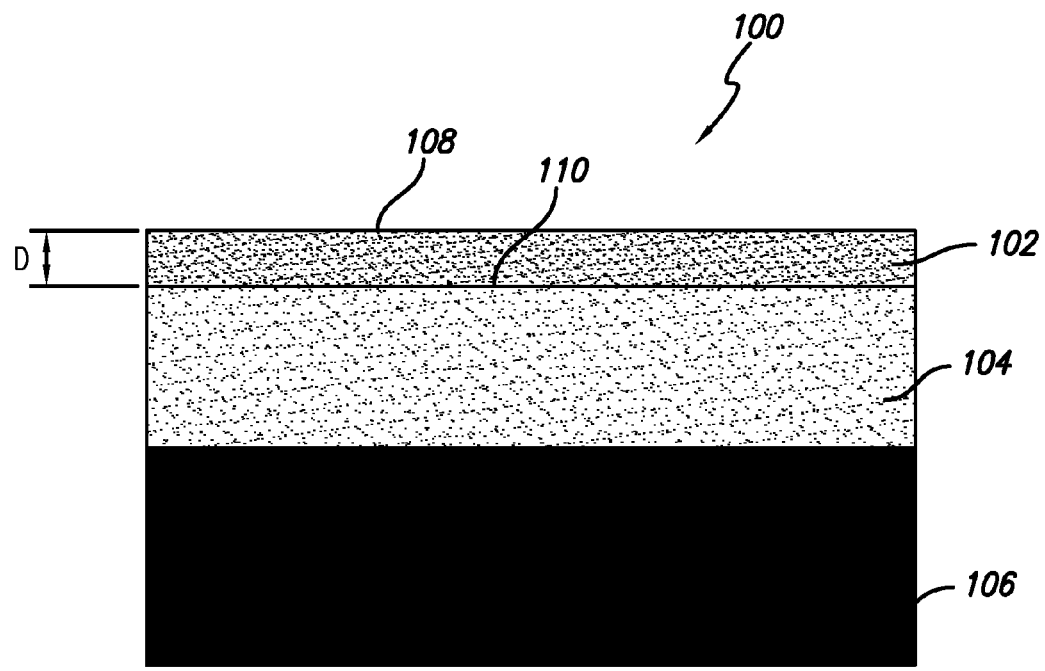
FIG. 7 is an X-ray image taken of an ultra-hard polycrystalline construction using the X-ray radioscopy device of FIG. 6.

FIG. 7 illustrates an image 100 provided by an XRR device as used to nondestructively measure the thickness of the construction first region 90. In an example embodiment, the image is one that is generated electronically from the X-ray radiation received from the construction and displayed on a suitable electronic display monitor. The image 100 provides an area plot of the construction volume, or in essence a shadow of the construction and its variation in density within the different construction regions.

In an example embodiment, the image 100 provided by the XRR device comprises a first image section 102 that corresponds to the construction first region 90, that is the lightest and that has the highest degree of exposure due to the absence of the catalyst material. The image 100 comprises a second image section 104 that corresponds to the construction second region 92, that that is relatively darker and that has a lower degree of exposure than the first region due to the presence of the catalyst material. The image 100 comprises a third image section 106 that corresponds to the construction substrate 94, that is relatively darker and that has a lower degree of exposure than the second region due to the heavy metal content in the substrate, e.g., when using a WC—Co substrate.

Because the X-ray radiation generated by the device 82 is directed radially through the entire diameter of the target construction, the different sections presented in the image 100 represent an average thickness of each of the respective regions within the construction. Once the XRR device is properly calibrated, e.g., using a standard construction having regions of known thicknesses, one is able to measure from the image the bulk thickness of each construction region. As used herein, the term "bulk thickness" is understood to mean the average thickness of the particular region for the part. Thus, a feature of using the XRR device and method for nondestructively measuring the construction is that, unlike the destructive test method that only provides region thickness information along a diametric section through the construction, its provides a projected area image of the construction and its different regions.

Another method that can be used to increase the of XRR is by narrowing the X-ray beam using a collimator or the like to produce a generally line-shaped beam as opposed to a pyramid or conical shaped beam. When the XRR device is configured in this manner, the line-shaped beam is generally aligned with a top surface of the object to be measured and the object is mounted on a precision translation table. The table is used to move the object vertically through the source beam, thus projecting a series of the plots to create an area plot of the targeted region with a much reduced geometric error. This system can be programmed to capture a transition zone within the object, e.g., between two adjacent regions within the object, and provide an output from a translation axis that can be correlated to the depth of the targeted region being measured.

If desired, to increase the statistical confidence that the image captures the average thickness of each construction region, the XRR device can be used multiple times with the construction being rotated, e.g., three images of the construction could be taken with the construction being rotated 120 degree for each image. Also, to increase statistical confidence, one can apply a computer tomography (CT) method to create a 3-D image of the construction. As illustrated in FIG. 7, the average thickness of the construction first region can be determined from the image by measuring the distance "D" from the surface 108 of the first image section 102 to the interface 110 with the second region 104.

This measurement can be performed manually by the user or can be done automatically, e.g., through the use of a computer software program such as one designed to calculate an average value from the electronic data representing an image section. In an example embodiment, the average value for a desired construction region thickness is determined automatically, e.g., through the use of such computer software. If desired, such software can further be configured to receive a user input, e.g., a target region thickness or the like, and provide a user output that compares the average measured thickness to the target thickness for the purpose of evaluating whether the construction conforms with the target thickness.

In an example embodiment, XRF is used as a first nondestructive method for measuring the thickness of a desired region within an ultra-hard polycrystalline construction that is part of a family of constructions that have been made using the same materials and by using the same process of manufacture. The exact number of parts within a can will vary on a number of factors such as the types of materials used to form the construction, the number of total needed parts needed for the end-use application, and the process that is used to form the parts.

The XRF device is used to obtain detailed measurement information along the region of the construction of interest. In an example embodiment, XRF is used to obtain a typographical plot of the region thickness to provide measurement information along a substantial area of the construction. This detailed measurement information is useful for determining whether the construction region thickness displays any unwanted irregularities that may operate to impair operating performance of the construction.

In an example embodiment, BB and/or XRR can be used as a second nondestructive method for measuring the thickness of a desired region within a number of the ultra-hard polycrystalline constructions or parts that are within the same family of the part that was measured using XRF. The use of such second nondestructive methods is desired for testing one or more of the remaining parts within the family of parts because these methods enable region thickness data to be obtained relatively quickly when compared to using XRF, thereby allowing for the efficient region thickness measurement of many parts, e.g., promoting use in a production environment.

In addition to BB and XRR, other nondestructive measurement methods can be used as a second nondestructive method for this invention, such as by eddy current (EC), magnetic induction (MI), and microresistance (MR).

Figure 8:
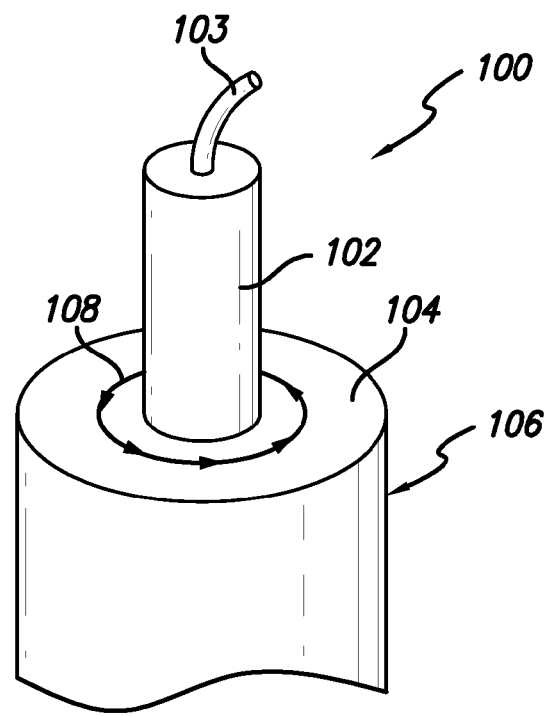
FIG. 8 is a schematic view of an eddy current device useful for determining the thickness and/or variation in thickness of a region within the ultra-hard polycrystalline constructions of FIGS. 1 and 2.

EC uses the principal of electromagnetism as the basis for conducting a nondestructive measurement of the target ultra-hard polycrystalline material. FIG. 8 illustrates an EC device 100 comprising a probe 102 that is positioned over a surface 104 of the object 106 to be measured, e.g., a surface of an ultra-hard polycrystalline construction, and is operated to generate eddy currents in the object through a process of electromagnetic induction. The probe 102 is connected to and alternating current (AC) source 103, and is operated to direct an alternating current (AC) magnetic field onto the object. This magnetic field expands as the alternating current rises to a maximum and collapses as the current is reduced to zero. When the object 106 is positioned in close proximity to the probe 102 and the changing magnetic field, eddy currents 108 will be induced in the object. Such eddy currents are induced electrical currents that flow in a circular path, and occur in the object 106 in proportion to the frequency of the AC magnetic field and resistivity of the object material. The induced eddy currents generate an opposing magnetic field that alters the circuit reactance and the output voltage of the probe 102. The change in output voltage is measured and is used to calculate the target region thickness in the object 106.

Figure 9:
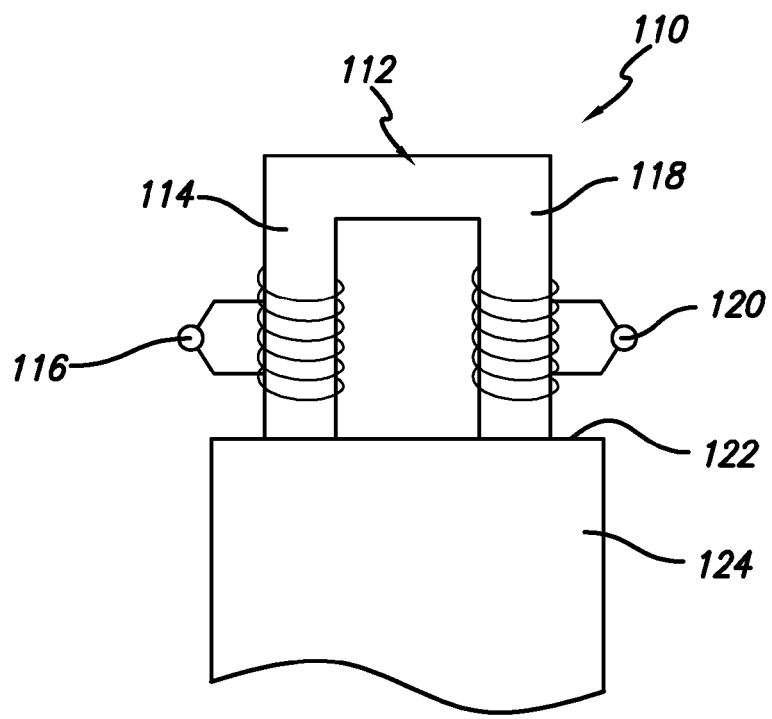
FIG. 9 is a schematic view of a magnetic induction device useful for determining the thickness and/or variation in thickness of a region within the ultra-hard polycrystalline constructions of FIGS. 1 and 2.

FIG. 9 illustrates a MI device 110 comprising a probe 112 in the form of a transformer circuit comprising a primary circuit 114 that is connected to an AC source 116, and a secondary circuit 118 that is connected to an amplifier or the like 120. The probe 112 is positioned adjacent a surface 122 of an object 124 to be measured. The system reacts to the presence of a target material in the object, e.g., a target material placed within a region of an ultra-hard polycrystalline material disposed beneath a surface region. The circuit efficiency and output voltage increase when the probe 112 is brought near the surface 122 of the object 124, providing parameters that can be used to measure the thickness of the region above the region containing the target material.

MR is a technique that can be used to determine the thickness of a region within an object, e.g., an ultra-hard polycrystalline material, from resistance calculations. Initially, precise resistance measurements are taken of an object having a known region thickness, e.g., a standard. Once this parameter is known, it is combined with other data from the object to calculate the average region thickness. These calculations can be performed automatically by software associated with the measurement device. Specially designed electrically isolated probe tips are then used to simultaneously inject current and take voltage drop measurements along the surface of the object to be measured. Resistance from these measurements is then calculated by Ohm's Law and are correlated to the standard to determine the measured thickness of the object.

While the nondestructive methods described herein have been described as being useful to measure the thickness of one or more regions within an ultra-hard polycrystalline material, and more specifically to measure the thickness of a region that is substantially free of catalyst material, it is to be understood that the nondestructive methods described herein can be used to measure the thickness of any region within such constructions. Such regions may or may not include a catalyst material. For example, the nondestructive methods described herein can be used to measure the thickness of one or more regions within the construction having the same general ingredients but different proportions of the ingredients. For example, when the ultra-hard polycrystalline construction is PCD, the nondestructive methods of this invention can be used to measure the thickness or one or more different PCD regions characterized by having different diamond volume contents.

Additionally, while the nondestructive methods of this invention have been described in the context of being useful to measure a region thickness extends a depth from a particular surface, e.g., a front side surface, of ultra-hard polycrystalline material, it is to be understood that the nondestructive methods of this invention can be used to measure region thicknesses that extend from other surfaces of the construction in addition to or apart from the construction front side surface. For example, nondestructive methods of this invention can be used to measure the region thickness extending from a beveled or chamfered surface of the construction that is oriented at an angle to the front side surface, and/or extending from a sidewall surface extending axially between the front side surface of the construction to the substrate.

The nondestructive methods described herein can be used to nondestructively measure the depth or thickness of one or more regions of ultra-hard polycrystalline constructions that are configured for use in a number of different applications, such as tools for mining, cutting, machining and construction applications. Such ultra-hard polycrystalline constructions are particularly well suited for forming working, wear and/or cutting components in machine tools and drill and mining bits such as roller cone rock bits, percussion or hammer bits, diamond bits, and shear cutters.

Figure 10:
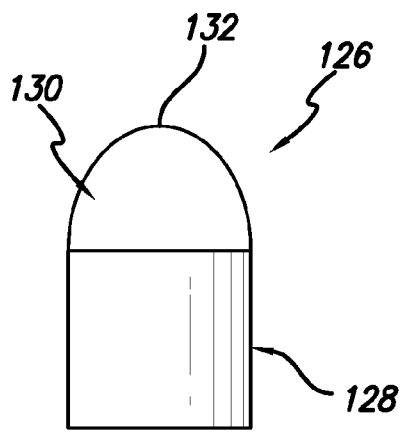
FIG. 10 is a perspective side view of an insert, for use in a roller cone or a hammer drill bit, comprising the ultra-hard polycrystalline construction measured using the nondestructive method of this invention.

FIG. 10 illustrates an embodiment of an ultra-hard polycrystalline construction, comprising one or more regions within the body that can be measured using the nondestructive methods described above, provided in the form of an insert 126 used in a wear or cutting application in a roller cone drill bit or percussion or hammer drill bit. For example, such inserts 126 are constructed having a substrate portion 128, formed from one or more of the substrate materials disclosed above, that is attached to a body 130 having first and second regions as described above. In this particular embodiment, the insert comprises a domed working surface 132, and the first region is positioned along the working surface and extends a selected depth therefrom into the body. In an example embodiment, the insert can be pressed or machined into the desired shape or configuration prior to the treatment for removing the catalyst material from the first region. It is to be understood that ultra-hard polycrystalline constructions can be configured as inserts having geometries other than that specifically described above and illustrated in FIG. 10.

Figure 11:
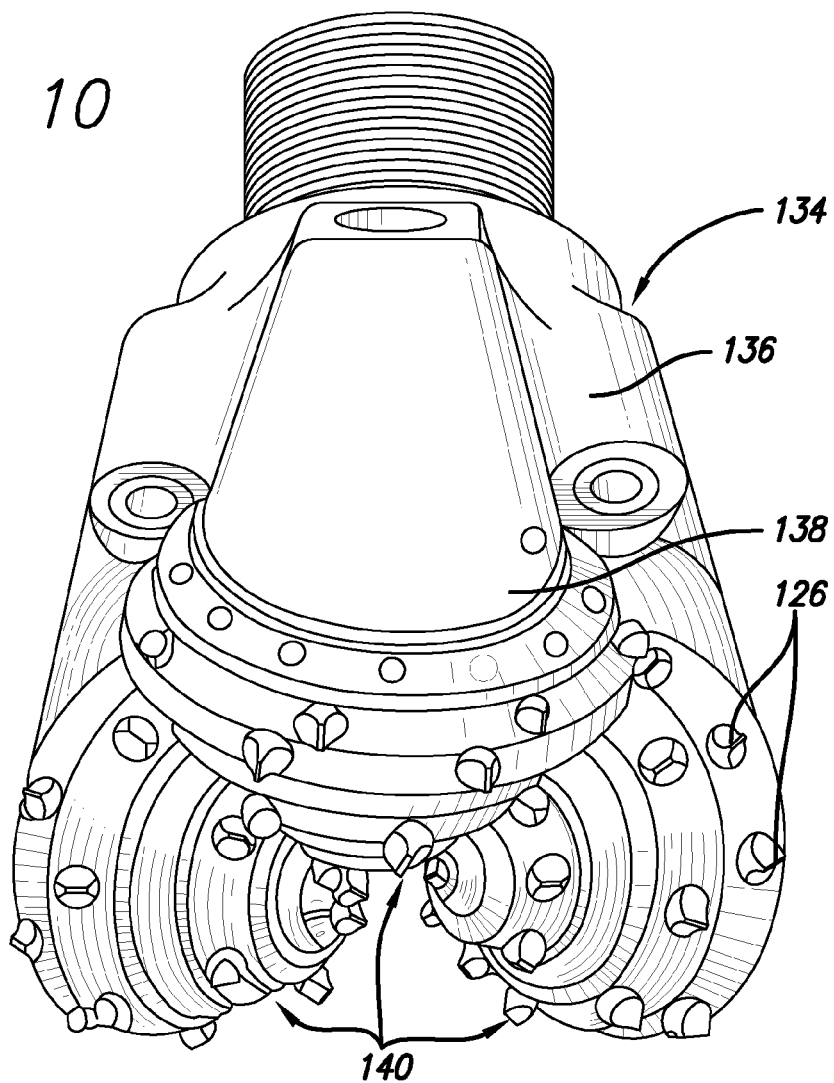
FIG. 11 is a perspective side view of a roller cone drill bit comprising a number of the inserts of FIG. 10.

FIG. 11 illustrates a rotary or roller cone drill bit in the form of a rock bit 134 comprising a number of the wear or cutting inserts 126 disclosed above and illustrated in FIG. 10. The rock bit 134 comprises a body 136 having three legs 138 extending therefrom, and a roller cutter cone 140 mounted on a lower end of each leg. The inserts 126 are the same as those described above comprising the ultra-hard polycrystalline construction, and are provided in the surfaces of each cutter cone 140 for bearing on a rock formation being drilled.

Figure 12:
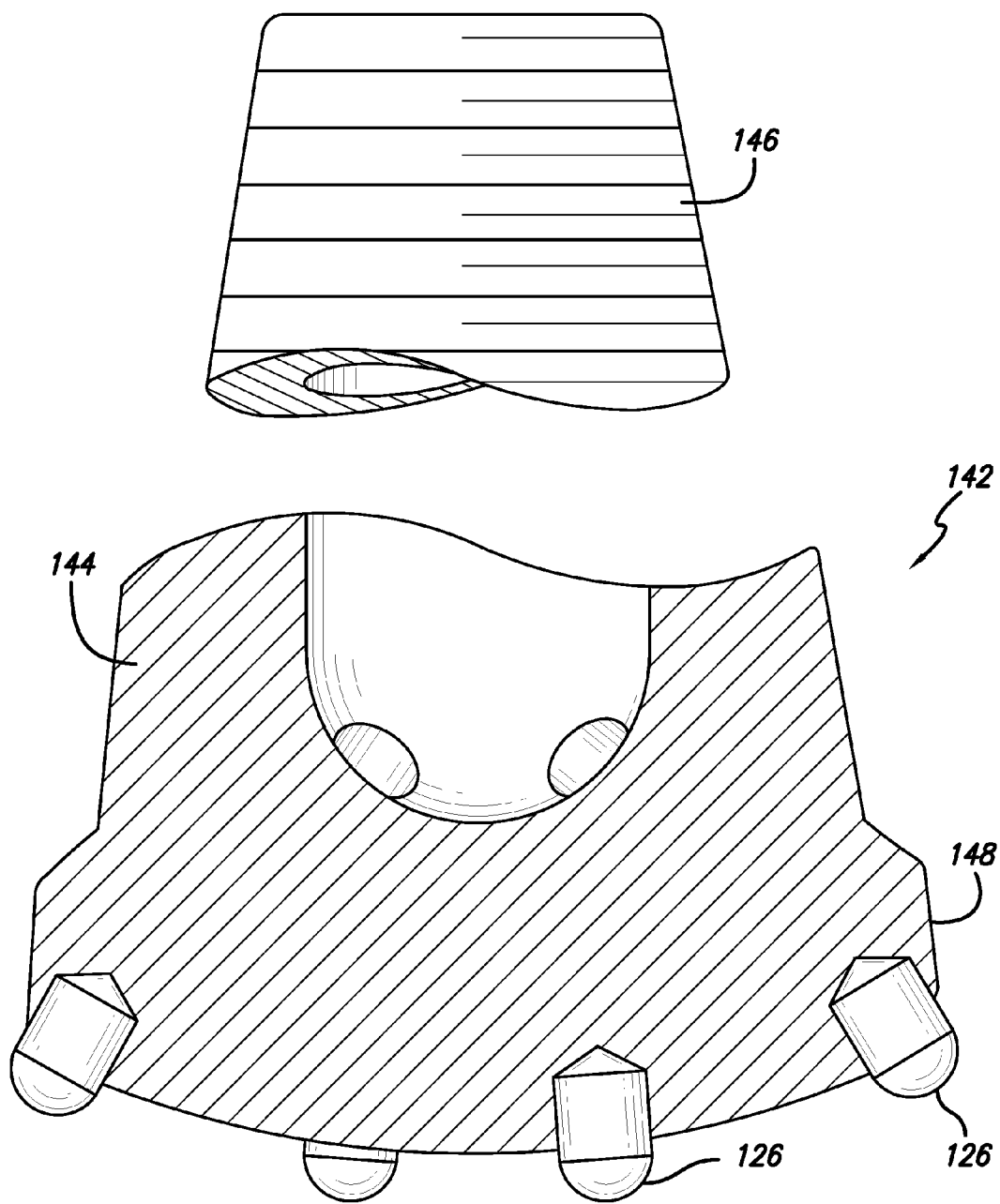
FIG. 12 is a perspective side view of a percussion or hammer bit comprising a number of inserts of FIG. 10.

FIG. 12 illustrates the insert 126 described above and illustrated in FIG. 10 as used with a percussion or hammer bit 142. The hammer bit generally comprises a hollow steel body 144 having a threaded pin 146 on an end of the body 144 for assembling the bit onto a drill string (not shown) for drilling oil wells and the like. A plurality of the inserts 126 are provided in the surface of a head 148 of the body 144 for bearing on the subterranean formation being drilled.

Figure 13:
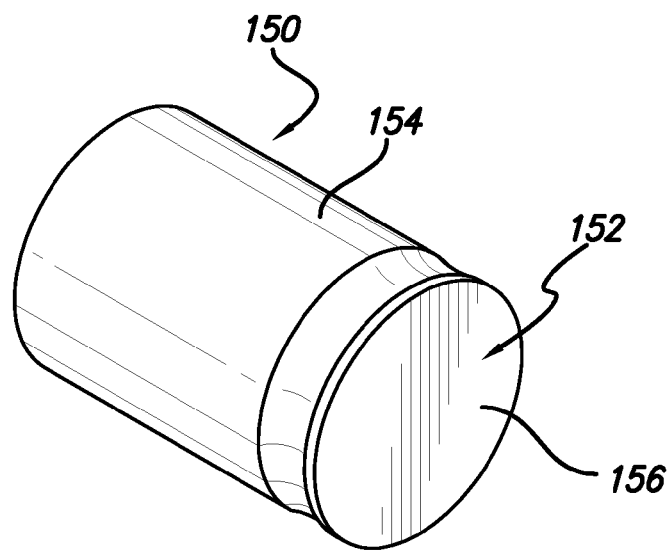
FIG. 13 is a schematic perspective side view of a shear cutter comprising the ultra-hard polycrystalline construction measured using the nondestructive method of this invention.

FIG. 13 illustrates an ultra-hard polycrystalline construction measured using the nondestructive methods described above as embodied in the form of a shear cutter 150 used, for example, with a drag bit for drilling subterranean formations. The shear cutter 150 comprises an ultra-hard polycrystalline body 152 that is sintered or otherwise attached to a substrate 154. The body 152 includes a working or cutting surface 156 that is formed from the construction first region. The working or cutting surface of the shear cutter can extend from the upper surface to a beveled surface defining a circumferential edge of the cutter and/or can extend along a sidewall surface of the cutter. The construction first region can extend a depth from such working surfaces. It is to be understood that ultra-hard polycrystalline constructions can be configured as shear cutters having geometries other than that specifically described above and illustrated in FIG. 13.

Figure 14:
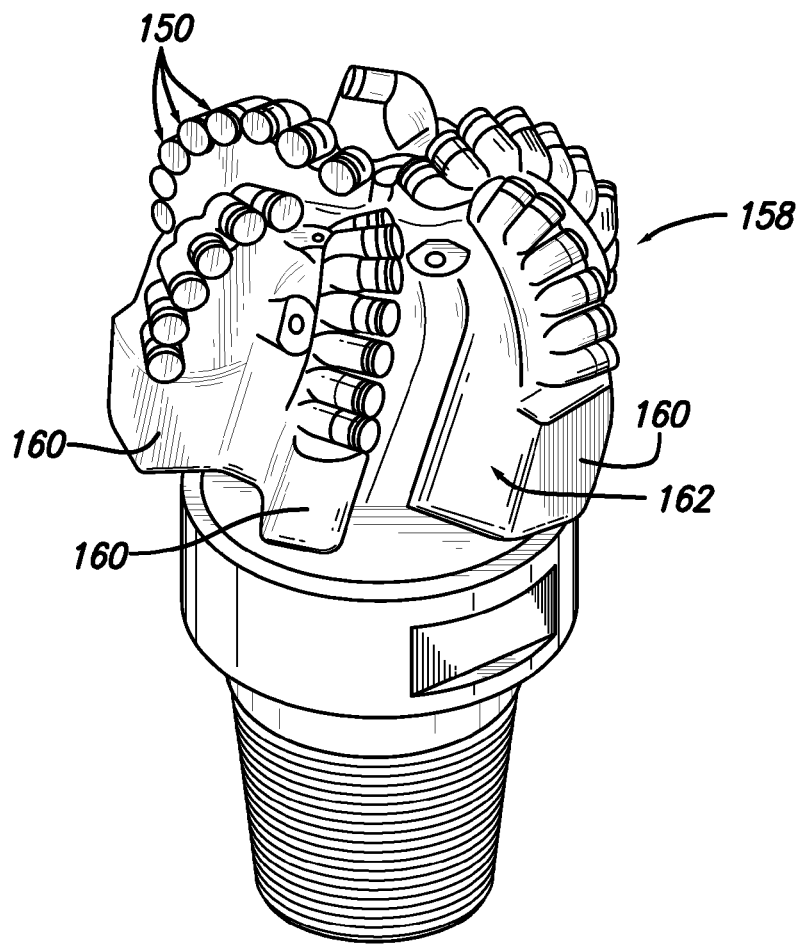
FIG. 14 is a perspective side view of a drag bit comprising a number of the shear cutters of FIG. 13.

FIG. 14 illustrates a drag bit 158 comprising a plurality of the shear cutters 150 described above and illustrated in FIG. 13. The shear cutters 150 are each attached to blades 160 that extend from a head 162 of the drag bit for cutting against the subterranean formation being drilled. Because the shear cutters of this invention include a metallic substrate, they are attached to the blades by conventional method, such as by brazing or welding.

Other modifications and variations of using nondestructive methods to measure the thickness or depth of one or more regions within ultra-hard polycrystalline constructions will be apparent to those skilled in the art. It is, therefore, to be understood that within the scope of the appended claims, this invention may be practiced otherwise than as specifically described.

The invention claimed is:

1. A method for nondestructively obtaining measurement information within a plurality of ultra-hard polycrystalline constructions, each ultra-hard polycrystalline construction comprising a polycrystalline diamond body, wherein the measurement information is of a region within the polycrystalline diamond body that comprises less catalyst material than present in another region of the polycrystalline diamond body, and wherein the method comprises the steps of:

conducting a first measurement using a device comprising an x-ray source and x-ray detector by directing x-rays generated by the source onto a surface of the body of one or more of the ultra-hard polycrystalline constructions, receiving x-ray fluorescence from the body, and deriving the measurement information from the received x-ray fluorescence; and using a nondestructive technique that is different than that used to conduct the first measurement to obtain a second measurement of one or more of the ultra-hard polycrystalline constructions;

wherein the measurement information is used to determine the thickness of the region comprising less catalyst material.

2. The method as recited in claim 1 wherein during the step of conducting the first measurement, the x-rays cause target atoms in the body to emit x-ray fluorescence, and wherein the region comprising less catalyst material comprises less target atoms.

3. The method as recited in claim 2 wherein the target atoms is a catalyst material selected from the group consisting of Group VIII elements of the Periodic table.

4. The method as recited in claim 1 wherein the step of conducting the second measurement is conducted using the techniques selected from the group consisting of beta backscatter, x-ray radioscopy, eddy current, magnetic induction, and microresistance.

5. The method as recited in claim 1 wherein the region comprising less catalyst material extends a depth from the surface of the diamond body.

6. A method for nondestructively obtaining measurement information within a diamond body of a plurality of ultra-hard polycrystalline constructions, wherein the diamond body includes a first region that extends a depth from a surface of the body and that is substantially free of a catalyst material, and a second region that extends from the first region and that includes the catalyst material, wherein the measurement information is used to determine the thickness of the first region, and wherein the method comprises the steps of:

conducting a first measurement using a device comprising an x-ray source and x-ray detector by directing x-rays onto a surface of the diamond body of one or more of the ultra-hard polycrystalline constructions, receiving x-ray fluorescence from the diamond body, and deriving the measurement information from the received x-ray fluorescence; and subjecting one or more of the ultra-hard polycrystalline constructions to a nondestructive technique selected from the group consisting of beta backscatter, x-ray radioscopy, eddy current, magnetic induction, and microresistance to obtain a second measurement;

wherein during the step of conducting a first measurement a map of measurement data is provided reflecting a measured surface area within the diamond body.

7. The method as recited in claim 6 wherein the surface area is disposed along an interface between the first and second regions.

8. The method as recited in claim 6 wherein during the step of conducting a first measurement, the x-ray fluorescence is emitted from a target atom that is present in the second region but not in the first region.

9. The method as recited in claim 6 wherein the target atom is selected from the Group VIII elements of the Periodic table.

10. The method as recited in claim 6 wherein the step of conducting a first measurement is repeated more than once to provide measurement information reflecting a desired surface area within the diamond body.

11. A method for nondestructively obtaining measurement information within a plurality of ultra-hard polycrystalline constructions, each ultra-hard polycrystalline construction comprising a polycrystalline diamond body, wherein the measurement information is of a region within the polycrystalline diamond body that comprises less catalyst material than present in another region of the polycrystalline diamond body, and wherein the method comprises the steps of:

conducting a first measurement using a device comprising an x-ray source and x-ray detector by directing x-rays generated by the source onto a surface of the body of one or more of the ultra-hard polycrystalline constructions, receiving x-ray fluorescence from the body, and deriving measurement information from the received x-ray fluorescence; and using a nondestructive technique that is different than that used to conduct the first measurement to obtain a second measurement of one or more of the ultra-hard polycrystalline constructions;

wherein during the step of conducting a first measurement an interface between the region comprising less catalyst material and an adjacent region of the diamond body is measured.

12. The method as recited in claim 11 further comprising generating a map of the interface from measurement information taken along a designated surface area.

* * * * *